United States Patent [19]

Johnson

[11] Patent Number: 5,190,033
[45] Date of Patent: Mar. 2, 1993

[54] ICE PEAS COLD/HOT THERAPEUTIC PACK

[76] Inventor: Linda J. Johnson, 1415 Eleventh Ave., San Francisco, Calif. 94122

[21] Appl. No.: 712,962

[22] Filed: Jun. 10, 1991

[51] Int. Cl.⁵ .............................................. A61F 7/00
[52] U.S. Cl. .................................. 128/403; 128/402; 128/380; 62/530
[58] Field of Search ............................ 228/399–403, 228/82.1, 24.1; 62/530, 4; 383/901

[56] References Cited

U.S. PATENT DOCUMENTS

| | | |
|---|---|---|
| H,759 | 4/1990 | Jones . |
| 2,472,754 | 6/1949 | Mead . |
| 2,547,886 | 4/1951 | Poux ................... 128/402 |
| 2,796,903 | 6/1951 | Gazelle ............... 128/402 |
| 3,212,497 | 10/1965 | Dickinson . |
| 3,762,404 | 10/1973 | Sakita . |
| 3,977,202 | 8/1976 | Forusz ................... 62/4 |
| 4,081,256 | 3/1978 | Donnelly ................ 62/4 |
| 4,243,041 | 1/1981 | Paul ..................... 128/402 |
| 4,325,230 | 4/1991 | Driscoll ................ 62/293 |
| 4,462,224 | 7/1984 | Dunshee et al. ...... 62/530 |
| 4,530,220 | 7/1985 | Nambu ................. 62/530 |
| 4,645,498 | 2/1987 | Kosak .................. 604/289 |
| 4,700,706 | 10/1987 | Munch .................. 128/403 |
| 4,756,311 | 7/1988 | Francis, Jr. .......... 128/403 |
| 4,910,978 | 3/1990 | Gordon et al. ........ 62/530 |

FOREIGN PATENT DOCUMENTS 2226956 7/1990 United Kingdom ............. 128/403

Primary Examiner—Mark Graham

[57] ABSTRACT

An improved cold/hot pack for physiotherapy having a completely sealed flexible pouch (16). The cavity of the pouch is filled with a plurality of approximately pea sized or larger hollow capsules (20). The cavities of the hollow capsules are filled with cold/hot storing fluid or gel (22). Partitions prevent migration of the capsules within the pouch and a screened plug permits air to be expelled from the pouch while the capsules are retained.

3 Claims, 6 Drawing Sheets

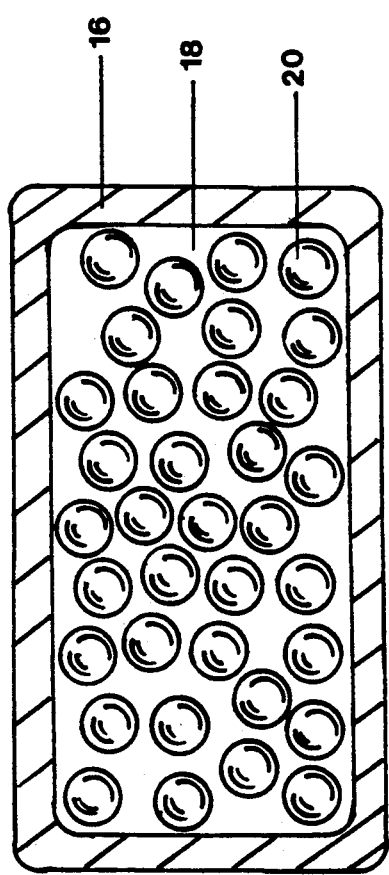
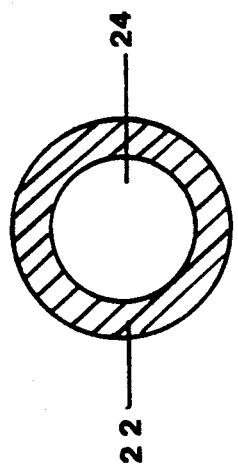
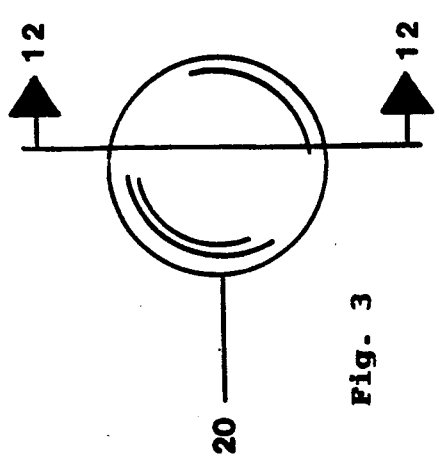

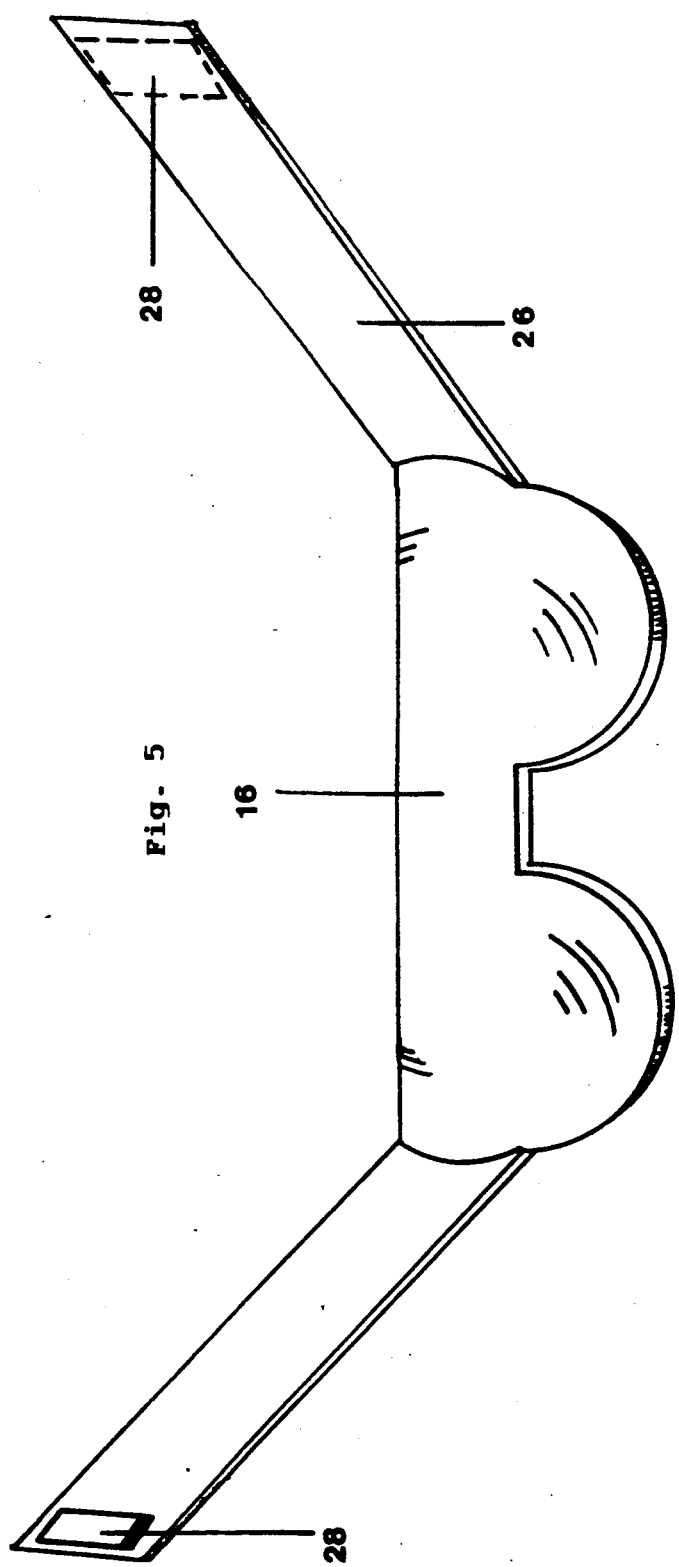

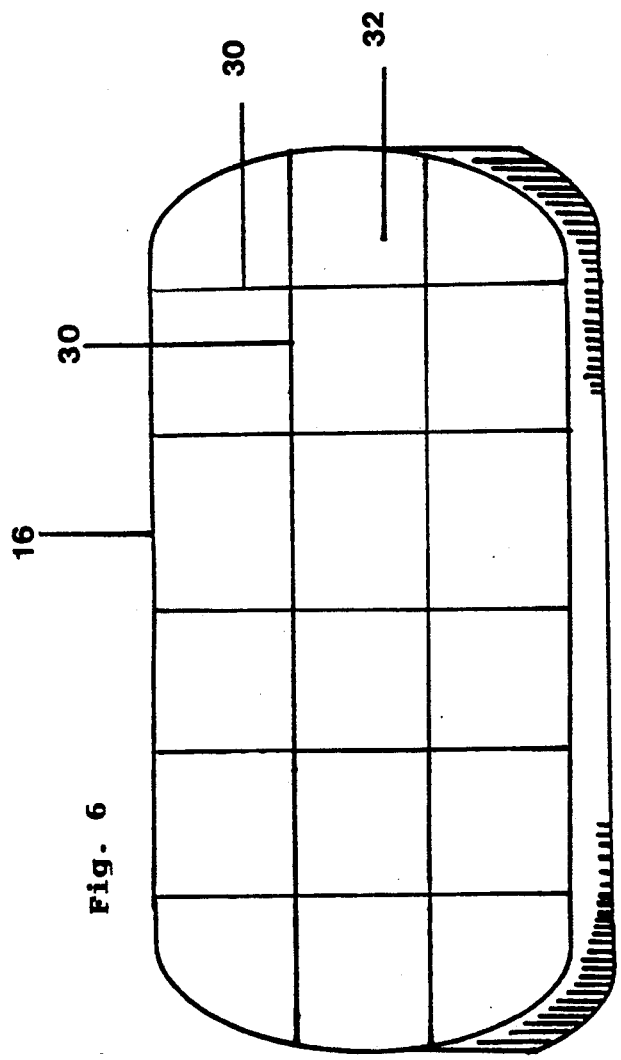

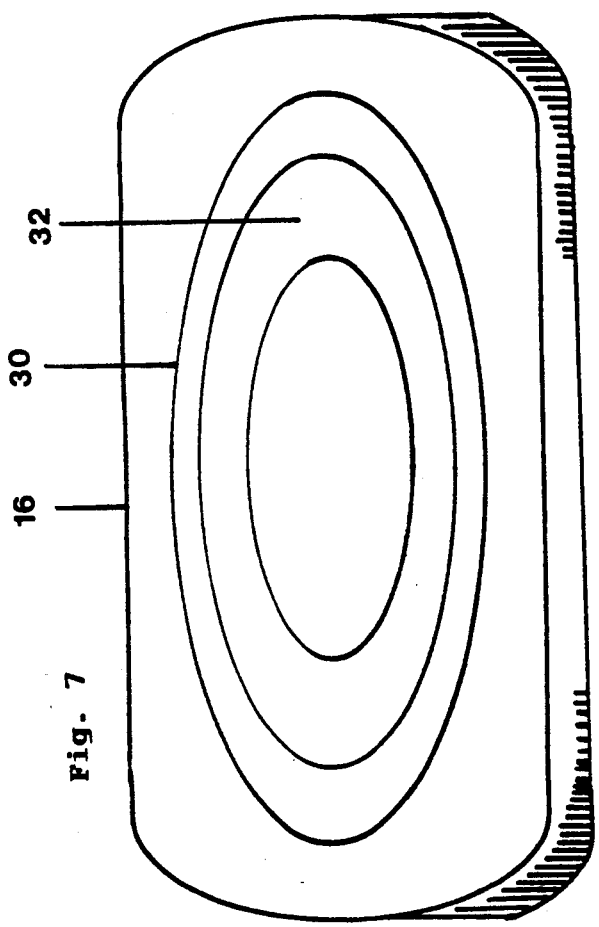

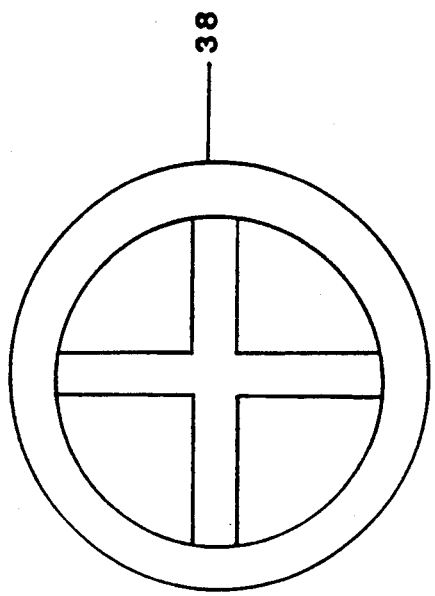
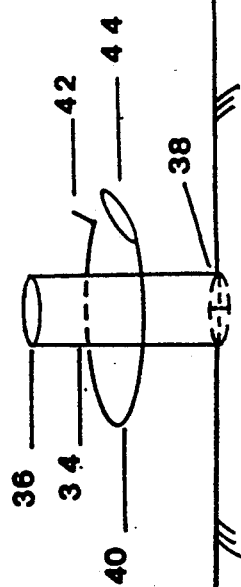
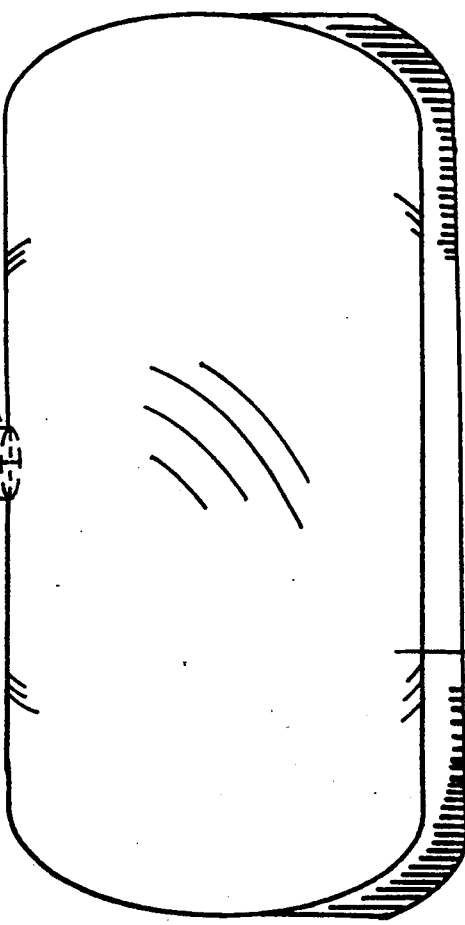

ICE PEAS COLD/HOT THERAPEUTIC PACK

BACKGROUND—FIELD OF INVENTION

This invention relates to cold/hot therapeutic packs, specifically to a pack which has an improved ability to conform totally to the natural contours of the body.

BACKGROUND—DESCRIPTION OF PRIOR ART

It has been conventional practice to treat post operative wounds, traumatic wounds, sports and other injuries with both cold and hot packs.

There are many benefits gained from this therapy.

When cold is applied to a wound, the blood vessels constrict. Circulation of blood to the treated body part is reduced. This results in decreased blood loss and bruising of the wound.

Reduced blood circulation to the wound also results in less leakage of and accumulation of fluid in the area. Less leakage of fluid results in a decrease of swelling of the injured area.

Reduced blood loss, bruising, and swelling lessen the disability of the patient and speed healing.

Application of cold also desensitizes nerve endings and thus helps to relieve pain.

Conversely, application of heat therapy speeds blood flow to the affected area. Special cells in the blood are allowed to kill bacteria, clean up the wound, remove by products created in the healing process, lay down new tissue, etc.

Heretofore, many attempts were made to create a therapeutic cold/hot pack which conformed to the natural contours of the body.

As this type of therapy has been used by professionals and lay people for perhaps centuries, many devices have been proposed to meet the needs of the patient.

One of the earliest proposed devices was a rubber bag which one filled with ice cubes or hot water. A version of this type of device was proposed by Kosak in U.S. Pat. No. 4,645,498 dated 1987. Filling a compress with a source of either cold or heat is inconvenient for the patient.

This fact was recognized and several other devices were proposed.

Many of these devices relied heavily on the use of chemicals such as the device of Forusz described in U.S. Pat. No. 3,977,202 of 1976 and the device of Donnelly described in U.S. Pat. No. 4,081,256 of 1978. Other disadvantages of these packs are that both of these packs can only be used as *cold* packs and are valueless in supplying any heat therapy.

My invention can be used as both a cold and a hot pack. A device proposed by Dunshee in U.S. Pat. No. 4,462,224 of 1984 shows a pack which relies heavily on chemicals for its operability and is only reusable as a *cold* pack.

My invention can be reused as both a cold and/or a hot pack. Thus, it is good for ecology. It can be cooled in a freezer or refrigerator, cold water bath, or by any other suitable method. It can be warmed in a microwave oven, warm water bath, or by any other suitable method. These processes may be repeated an infinite number of times.

My invention can be manufactured using little or no chemicals. It can be made out of non-toxic plastic and water.

The impact of the use of chemicals on human health and on the environment is not fully known and understood. Nambu in U.S. Pat. No. 4,530,220 of 1985 shows a device which proposes the possible use of approximately 45 different chemicals in its manufacture.

The process for manufacturing this device appears complicated. For example, the degree of hydrolysis must be a certain percentage or the gel may be weak and crumble, the strength of the gel may be lowered, or the gel may become too hard and uncomfortable to the touch.

The manufacture of this device requires many different processes wherein concentration of all of these chemicals, percentage dehydration rate, cooling of the cast mass, etc. must all be controlled accurately.

Also, the small pieces of gel could, due to gravitational force, sag and migrate off the wound. No means are suggested to keep these pieces of gel in proper position on the wound.

There is no indication that Nambu's pack can be used for heat therapy.

The use of packs containing gel was proposed: in U.S. Pat. No. 4,756,311 of 1988 by Francis, U.S. Pat. No. 4,462,224 of 1984 by Dunshee, U.S. Pat. No. 4,910,978 of 1990 by Gordon, U.S. Pat. No. 4,700,706 of 1987 by Munch, and in U.S. Pat. No. 4,243,041 1981 by Paul.

Gel, however, does *not* conform to the natural contours of the body. A space remains between the pack and the underlying tissue. The therapeutic effect of the cold or heat of the pack is diminished. My invention conforms totally to the natural contours of the body.

Also, the devices of Gordon, Paul, and Jones cannot be used as warm packs.

My invention can be used for both cold and warm therapy. It even can be placed in a microwave oven to warm it. The device of Munch cannot be warmed in a microwave because it has a component made of foil.

Any device which has been patented and/or which is on the market and is composed of gel does *not* conform totally to the natural contours of the body. This was realized perhaps by Jones in U.S. Statuatory Invention Registration No. H759 of 1990—as evidenced by his attempt to compensate for the disadvantage of gel packs by placing gel into compartments. It was hoped that these *compartments* of gel would conform to the contours of the body. Hinges are formed between the peripheral edges of each compartment. It is hoped that these compartments and hinges will allow the pack to completely conform to the the contours of the underlying body part.

However, these hinges are only able to bend where they are placed in the pack. For example, the body part may contour, but if no hinge is provided at that spot, there will be non-conformity, and a space will remain between the wound and the pack.

Anyone who has ever sat on a "Bean Bag" chair can attest to the confort such chairs provide. The beans inside the bags are highly mobile and arrange themselves into a perfect mold of the shape of the body. When one gets up from the chair and looks down at it, one can see the perfect impression of his body still left in the chair.

This is the principle behind my cold/hot pack. My pack contains a plurality of hollow capsules. Experimentation has shown that the best size for these capsules is a largest dimension of about one half inch or smaller. The capsules should preferably be spherical in shape, but other shapes may be used. The capsules may be randomly shaped. These specifications should not be construed as limitations on the scope of the invention, but rather as an exemplification of some preferred embodiments thereof.

The capsules act like the beans in a bean bag chair. When placed on a patient, the capsules move around and arrange themselves into a perfect conformation of the underlying body part. There is total contact of the pack with the underlying tissue, and thus a more even and efficient transfer of cold or heat to the injured part. This results in increased therapeutic benefit.

The cavities of these capsules contains a temperature storing substance. The thin walls of the capsules efficiently transfer coldness or warmth to the tissues of the body.

This pack is particularly well suited for used on the sockets of the eyes. My invention in the embodiment of an eye pack is my preferred practical application. Eye holes may be provided in the eye pack for the patient to see through while wearing the pack.

Paul, in U.S. Pat. No. 4,243,041 1981, shows a cold pack in the shape of goggles for use on the eyes. However, this pack contains gel. Gel does not conform perfectly to the natural contour of the underlying tissue. A space remains between the pack and the body part. Thus, there is no contact between the cold or warmth of the pack and the underlying tissue. There is non-uniform contact and non-uniform cold/heat transfer. Therapeutic benefit is decreased.

My invention is durable, light weight and inexpensive to manufacture (allowing affordability for all patients). Different sizes and shapes may be manufactured to suit different parts of the body. It is safe and easy to use. Therefore, my cold/hot pack provides all the advantages of previously patented cold/hot packs plus it provides a greater therapeutic benefit because it has a greater ability to conform to the natural contours of the body.

OBJECTS AND ADVANTAGES

Accordingly, besides the objects and advantages of the cold/hot pack described in my above patent, several objects and advantages of the present invention are:

(a) a primary object of my invention is to provide a heightened therapeutic benefit in use of cold/hot packs due to my invention's superior ability to conform perfectly to the natural contours of body parts and especially to the sockets of the eyes;

(b) to provide a cold/hot pack which is reusable;

(c) to provide a cold/hot pack which is easy to use— one that can be warmed in a microwave oven, hot water bath, or by any other suitable method;

(d) to provide a cold/hot pack which is easy to use— one that can be chilled in a refrigerator or freezer, cold water bath, or by any other suitable method;

(e) to provide a cold/hot pack which does not rely on heavy use of chemicals for its function or manufacture;

(f) to provide a cold/hot pack which can be used for both cold and hot therapy;

(g) to provide a cold/hot pack which is light weight, durable, economical to manufacture, and inexpensive to purchase;

(h) to provide a cold/hot pack which can be varied in size and in shape in order to adapt to all parts of the human or animal body;

(i) to provide a pack which reaches the desired therapeutic temperature and maintains this temperature for an adequate duration of time.

Further objects and advantages will become apparent from a consideration of the ensuing description and drawings.

DRAWING FIGURES

FIG. 2 shows a cross sectional view of my invention taken along line 10 of FIG. 1. This cross sectional view of my invention's pouch is valid for all the embodiments of my invention described in this patent.

FIG. 3 shows a view of a capsule.

FIG. 4 is a cross sectional view of a capsule taken through line 12 of FIG. 3.

FIG. 5 is a perspective view of one embodiment of my invention in which the pouch has been manufactured into a goggle shape for use on the eyes.

FIG. 6 is a perspective view of one embodiment of my invention in which compartments have been formed in the pack in a grid shaped pattern.

FIG. 7 is a perspective view of one embodiment of my invention in which compartments have been formed in the pack in a circular pattern.

FIG. 8 is a perspective view of one embodiment of my invention in which an air exhaust tube, an air exhaust aperture, and means of reversably sealing this air exhaust tube are provided.

FIG. 9 is a top view of means for allowing passage of air while retaining capsules.

REFERENCE NUMERALS IN DRAWINGS

Figure 1:
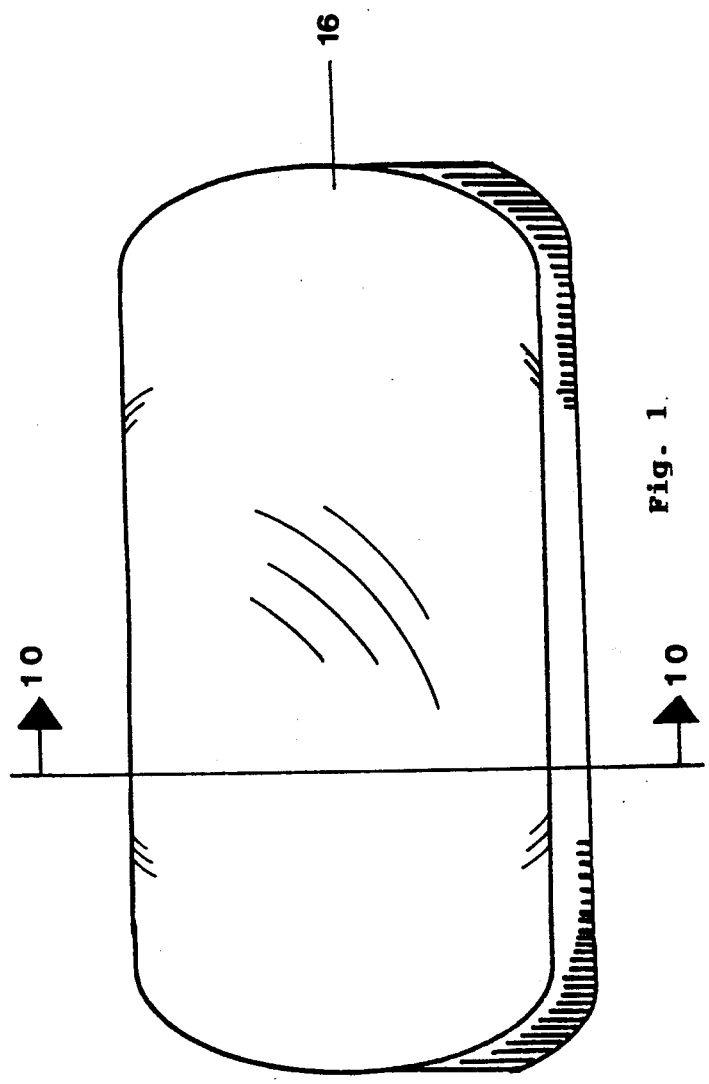
FIG. 1 shows a perspective view of one embodiment of my invention.

16: pouch
18: cavity of pouch
20: hollow capsule
22: wall of capsule
24: cavity of capsule containing a temperature storing substance
26: strap
28: means of removably securing one end of the strap to the other end of the strap
30: means of creating compartments in the pouch
32: compartments
34: air passage tube
36: air passage tube aperture
38: means for allowing passage of air while retaining capsules
40: air passage tube clamp
42: air passage tube clamp hook portion
44: air passage tube clamp eye portion

DESCRIPTION —FIGS. 1 to 9

FIG. 1 shows a perspective view of a pouch 16 constructed from flexible, pliable material.

FIG. 2 is a cross-sectional view of the pouch 16 shown in FIG. 1 taken along line 12. The cavity of the pouch 18 is filled with a plurality of hollow capsules 20.

FIG. 3 shows a capsule 20.

FIG. 4 is a cross-sectional view of a capsule 20 taken along line 14 of FIG. 3. Each capsule 20 has a wall 22 and a cavity containing a temperature storing substance 24.

FIG. 5 is a perspective view of one embodiment of my invention in which the pouch 16 has been manufactured into a goggle shape. Straps 26 have been provided to secure the pack to the body. Means for removably securing one end of the strap to the other end of the strap 28 are provided.

FIG. 6 shows an embodiment of my invention in which means of creating compartments in the pouch 30 have been provided.

The compartments 32 have been formed in the pouch in a grid shaped pattern.

FIG. 7 shows an embodiment of my invention in which means of creating compartments in the pouch 30 are provided. The compartments 32 have been formed in the pouch in a circular pattern.

FIG. 8 shows an embodiment of my invention in which an air passage tube 34 is provided. This tube has been provided with an air passage tube aperture 36. Means for allowing passage of air while retaining capsules 38 is provided. An air passage tube clamp 40 is provided with both a hook portion 42 and an eye portion 44.

FIG. 9 shows a top view of means for allowing passage of air while retaining capsules 38. The means of capsule retention are encircled by the wall of the air passage tube 34.

OPERATION—FIGS. 1 THROUGH 9

FIG. 1 shows a basic embodiment of my invention. A pouch 16 is constructed from flexible, pliable material. Its peripheral edges are sealed on three side by such means as heat sealing, stitching, etc. Hollow capsules 20 as shown in FIG. 3 may be molded from a material such as plastic. The cavities of these hollow capsules are filled with a temperature storing substance 24 such as a gel or fluid as shown in FIG. 4. The capsules may be filled by injection. The injection holes may be sealed by using a heat process. Next the cavity of the pouch is filled with a plurality of capsules as shown in FIG. 2. Finally, the fourth peripheral edge of the pouch may be sealed by such means as heat sealing, etc.

The cold/hot pack of my invention is chilled in a freezer or refrigerator, or it is warmed in a microwave oven, warm water bath, etc. After reaching the required temperature, the pack is placed on a body part. The highly mobile capsules move around and conform themselves to the natural contours of the treated body part. When the pack has returned to room temperature, the process is repeated as often as desired.

On some body parts, the capsules may be affected by gravity and could migrate off of the wound. FIGS. 6 and 7 show that means of creating compartments in the puch 30 have been provided. The means of creating the compartments can include lines of stitching, heat sealing, etc. The compartments 32 will help to arrest the migration of the capsules. FIG. 6 shows the compartments arranged in a grid pattern. FIG. 7 shows the compartments arranged in a circular pattern. Two patterns for compartments have been shown. Many other variations are possible. These specifications should not be construed as limitations on the scope of the invention, but rather as an exemplification of some preferred embodiments thereof.

The compartments of my invention are superior in function to those of Jones in U.S. Statutory Invention Registration No. H759 of 1990. Although my compartments restrict the movement of the capsules somewhat, the capsules retain their superior ability (as opposed to gel) to conform to the wound or injury. The capsules are still capable of molding perfectly to the contours of the body.

FIG. 8 shows a cold/hot pack of my invention in which the pouch 16 is provided with an air passage tube 34. The air passage tube has an aperture 36 and a clamp 40 for reversably sealing the tube. The clamp may be produced by molding it out of metal or some other such method and material.

The pack is placed on the injured body part. The pack molds itself perfectly to the natural contours of the body. Gentle pressure on the pack causes the air to be expelled from the pack through the aperture of the tube. Means of allowing the passage of air while retaining the capsules are provided 38. These means may be made of a microwavable material and may be in the configuration of a screen—or in the shape of an X or a cross. The means for allowing passage of air while retaining capsules 38 may be molded from plastic—or another suitable method and material may be used. Many other variations are possible. These specifications should not be construed as limitations on the scope of the invention, but rather as an exemplification of some preferred embodiments thereof.

After air is expelled from the pack, the hook portion of the air passage tube clamp 42 is inserted through the eye portion of the air passage tube clamp 44. This reversably closes the tube and keeps air from re-entering the pouch.

When air is expelled from the pouch, the capsules clump together and become immobile.

Thus, the pack with air in it (in its highly mobile, fluid state) is placed on the wound where it assumes the shape of the body part. The air is expelled and the pack becomes a solid, unmoving mass in the shape of a perfect impression of the body part. This provides total contact of the pouch with the body part and thus the cooling/warm therapeutic benefits of the pack are maximized. The capsules are immobilized, and there can be no migration of the capsules off the wound. This principle is demonstrated by the bean bag positioning device used in operating rooms.

Alternately, the pack may be placed on the body and a bandage may be wrapped around both the pack and the body part. The pressure of the bandage being wound around the body part will express the air from the pouch When it is time to remove the pack, the clamp is opened by releasing the hook portion of the clamp from the eye portion. Air re-enters the pack. The pack regains its pliability and can be molded into a new configuration for another part of the body.

Other means may be employed to insert air, remove air, retain air, retain capsules while air is being expelled from the pack, or to keep the tube closed. These specifications should not be construed as limitations on the scope of the invention, but rather as an exemplification there of. Many other variations are possible.

For example, the mouth can be used on the exhaust tube to either insert air or to remove air by suction.

Means such as those employed in the currently popular "pump" athletic shoes may be used.

Means used in the design and function of a penile prosthesis may be employed.

In a hospital setting, wall suction may be employed to remove air from the pouch. This embodiment is especially valuable when used on burn or trauma patients. The pack could be made large enough to treat an entire limb.

A special valve may be used which when squeezed causes air to re-enter the pack.

A cap could be placed on the end of the tube in place of the air passage tube clamp.

Instead of an air passage tube, vents may be provided in the pouch. When the pouch is arranged on the body part, gentle pressure may be used to express air from the pack through these vents.

Packs may be made in different sizes and shapes for different body parts or for the entire body.

Various microwave safe materials may be used in the manufacture of this pack.

Temperature storing fluid *or* gel may be used inside the capsules.

Many other variations are possible. Although the description above contains many specificities, these should not be construed as limiting the scope of the invention but as merely providing illustrations of some of the presently preferred embodiments of this invention.

CONCLUSION, RAMIFICATIONS, AND SCOPE OF INVENTION

Accordingly, the reader will see that the cold/hot pack of the invention provides a highly reliable, light weight, economical, easy to use, reusable, non-chemical dependent device which maximizes therapeutic benefit by providing perfect conformity and contact of the pack with the body part.

Although the description above contains many specificities, these should not be construed as limiting the scope of the invention but as merely providing illustrations of some of the presently preferred embodiments of this invention.

For example, a bandage made of an elastic material can be attached to one edge of the pack. At the opposite edge of the pack can be a slot equal in width to the bandage. The pack can be placed on a body part (such as an extremity). The bandage can then be passed behind the extremity, through the slot at the opposite edge of the bandage, across the front of the pack, around the extremity again, and then removably fastened to itself. This is the most efficient way to secure a pack to a body part and to keep the pack in the proper position.

Thus the scope of the invention should be determined by the appended claims and their legal equivalents, rather than the examples given.

I claim:

1. A method of providing heat or cold therapy to a selected body part of a patient comprising:
   (a) providing a therapeutic pack at a desired temperature, said pack comprising:
      (i) a pouch readily deformable over a therapeutic range of temperatures,
      (ii) a plurality of hollow capsules disposed within said pouch, said capsules encapsulating means stable over a therapeutic range of temperatures for retarding temperature change of said capsules once said capsules are at a desired temperature,
      (iii) plug means for controlled movement of air into and out of said pouch;
   (b) positioning said pack in conformable relation over a contour of the body part;
   (c) removing air from said pack through said plug means to immobilize said pack in its contact configuration with the body part.

2. The method of claim 1 wherein said pouch of the therapeutic pack is provided with means for partitioning said capsules into at least two contiguous chambers within said pouch to prevent uncontrolled migration of said capsules within said pouch.

3. A deformable therapeutic pack for delivering heat or cold to a selected body part of a human or animal, said deformable pack capable of immobilized conformity with a contour of the body part, said pack comprising:
   (a) a pouch readily deformable over a therapeutic range of temperatures, said pouch provided with means for partitioning said pouch into at least two contiguous chambers to prevent uncontrolled migration of said capsules within said pouch;
   (b) a plurality of capsules disposed within each of the chambers of said pouch, said capsules encapsulating means for retarding temperature change of said capsules from a desired capsule temperature;
   (c) plug means for controlled movement of air into and out of said pouch, said plug means comprising a tube coupled to an opening in said pouch and fitted with a screen to retain said capsules within said pouch but through which air may freely pass.

* * * * *